United States Patent
Mandal et al.

[11] Patent Number: 6,041,861
[45] Date of Patent: Mar. 28, 2000

[54] METHOD TO DETERMINE SELF-CALIBRATED CIRCUMFERENTIAL CASED BOND IMPEDANCE

[75] Inventors: Batakrishna Mandal, Missouri City; Thomas E. Standley, Magnolia, both of Tex.

[73] Assignee: Halliburton Energy Services, Inc., Houston, Tex.

[21] Appl. No.: 08/992,608

[22] Filed: Dec. 17, 1997

[51] Int. Cl.$^7$ .............................. E21B 47/12; G01V 1/40
[52] U.S. Cl. .................. 166/250.01; 166/254.2; 166/253.1; 367/35
[58] Field of Search ................. 166/250.01, 254.2, 166/253.1, 254.1; 367/35, 30

[56] References Cited

U.S. PATENT DOCUMENTS

| | | | |
|---|---|---|---|
| 4,131,875 | 12/1978 | Ingram | 340/15.5 BH |
| 4,218,766 | 8/1980 | Parrack et al. | 367/47 |
| 4,685,092 | 8/1987 | Dumont | 367/35 |
| 4,703,427 | 10/1987 | Catala et al. | 364/422 |
| 4,928,269 | 5/1990 | Kimball et al. | 367/35 |
| 5,089,989 | 2/1992 | Schmidt | 367/35 |
| 5,216,638 | 6/1993 | Wright | 367/35 |

*Primary Examiner*—Frank Tsay
*Attorney, Agent, or Firm*—Conley, Rose & Tayon

[57] ABSTRACT

A method and device are disclosed for determining the impedance of the cement bond between a borehole casing and its wellbore. The invention uses a predicted resonance response as a baseline for determining from the observed resonance response the approximate impedance of the cement. Corrections are made to account for various defects in the casing by normalizing the received resonance response.

32 Claims, 10 Drawing Sheets

METHOD TO DETERMINE SELF-CALIBRATED CIRCUMFERENTIAL CASED BOND IMPEDANCE

CROSS-REFERENCE TO RELATED APPLICATIONS

Not Applicable.

STATEMENT REGARDING FEDERALLY SPONSORED RESEARCH OR DEVELOPMENT

Not Applicable.

BACKGROUND OF THE INVENTION

1. Field of the Invention

The present invention relates generally to oil well drilling. More particularly, the present invention relates to determining the quality of the bonding between a downhole casing and the surrounding formation. Most particularly, the present invention relates to a new system and method for obtaining an impedance measurement of the cement bonding between a downhole casing and the surrounding formation.

2. Description of the Related Art

Although oil well production has been a boon to mankind, with it has come certain deleterious side effects. One problem known in oil field drilling is the contamination of fresh water aquifers by hydrocarbon deposits explored by a wellbore. That is, when an oil well borehole is drilled through both an aquifer and a hydrocarbon region, there exists a risk that hydrocarbons will flow from the hydrocarbon region to the aquifer. This contamination can have a significant negative impact on the environment and upon drinking water.

FIG. 1 illustrates the occurrence of such contamination. The surface of the earth 100, a borehole 110 passing through a rock lithology 160 including an aquifer region 120 and an oil region 130, a steel casing 140 residing in the borehole, and cement 150 bonding the casing 140 to the surrounding formation 160 are pictured. The steel casing 140 is provided around the periphery of the borehole 110 after drilling the well, in part to prevent the collapse of the well. This steel casing is held in place by special cement 150. If the cement has proper bonding, the risk of oil flow 170 from the hydrocarbon deposits to the aquifer region is reduced significantly. If, however, the casing is improperly bonded, the risk that contamination may occur is much greater.

It has been found that a casing's bonding properties correspond to the impedance of the cement bonding the casing to the surrounding formation. The cement impedance indicating proper bonding varies depending upon the type of cement used. Nonetheless, where the cement has an impedance of less than 3, there exists poor bonding. At about an impedance of 3, adequate bonding has been achieved. Preferable bonding, however, has an impedance on the order of 4 to 5 for soft cement, and 5 to 6 for hard cement. Therefore, an invention capable of determining the impedance of the bonding would be useful to those searching for ways to determine the bonding properties. Further, such an invention could be used to evaluate cementing techniques so that more effective methods of cementing the casing to the formation may be developed.

Some efforts have been made to determine by acoustic tools the bonding properties of casing. Nonetheless, there still exists a need for an alternative, fast, and reliable device and method to determine the quality of the bond between the casing and the formation surrounding the borehole.

SUMMARY OF THE INVENTION

A simplified interpretation of the teachings disclosed herein is that the present invention finds cement impedance, and therefore the quality of the casing bond, by mathematically fitting predicted theoretical reverberation responses with the measured reverberation responses. Because the reverberation characteristics of an acoustic wave depend in part on the impedance of the cement bonding, the impedance of the cement may be closely approximated.

Thus, the present invention comprises a combination of features and advantages which enable it to overcome various problems of prior devices. The various characteristics described above, as well as other features, will be readily apparent to those skilled in the art upon reading the following detailed description of the preferred embodiments of the invention, and by referring to the accompanying drawings.

BRIEF DESCRIPTION OF THE DRAWINGS

For a more detailed description of the preferred embodiment of the present invention, reference will now be made to the accompanying drawings, wherein.

DETAILED DESCRIPTION OF THE PREFERRED EMBODIMENT

Figure 1:
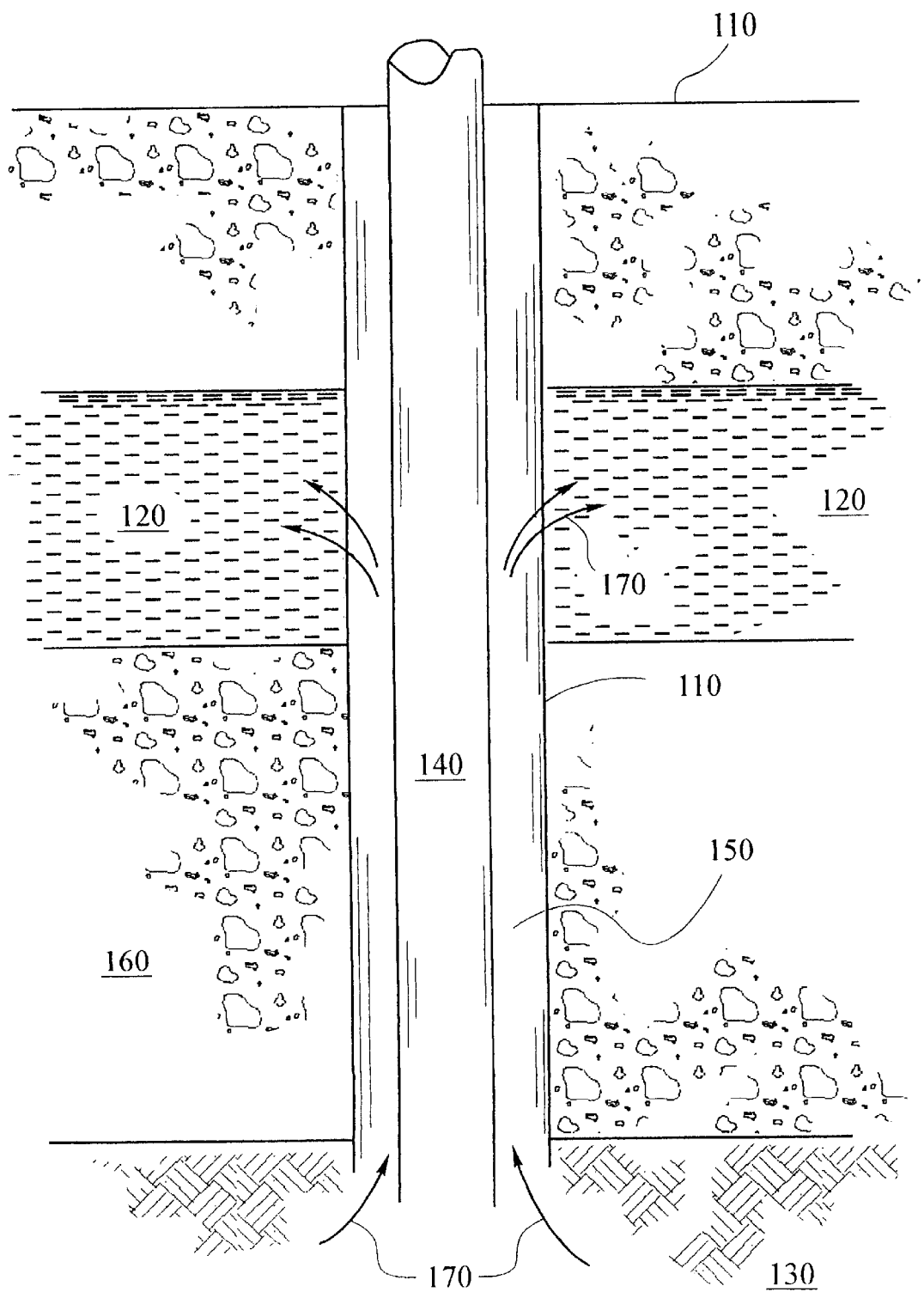
FIG. 1 illustrates a leak of hydrocarbons to an aquifer
Figure 2:
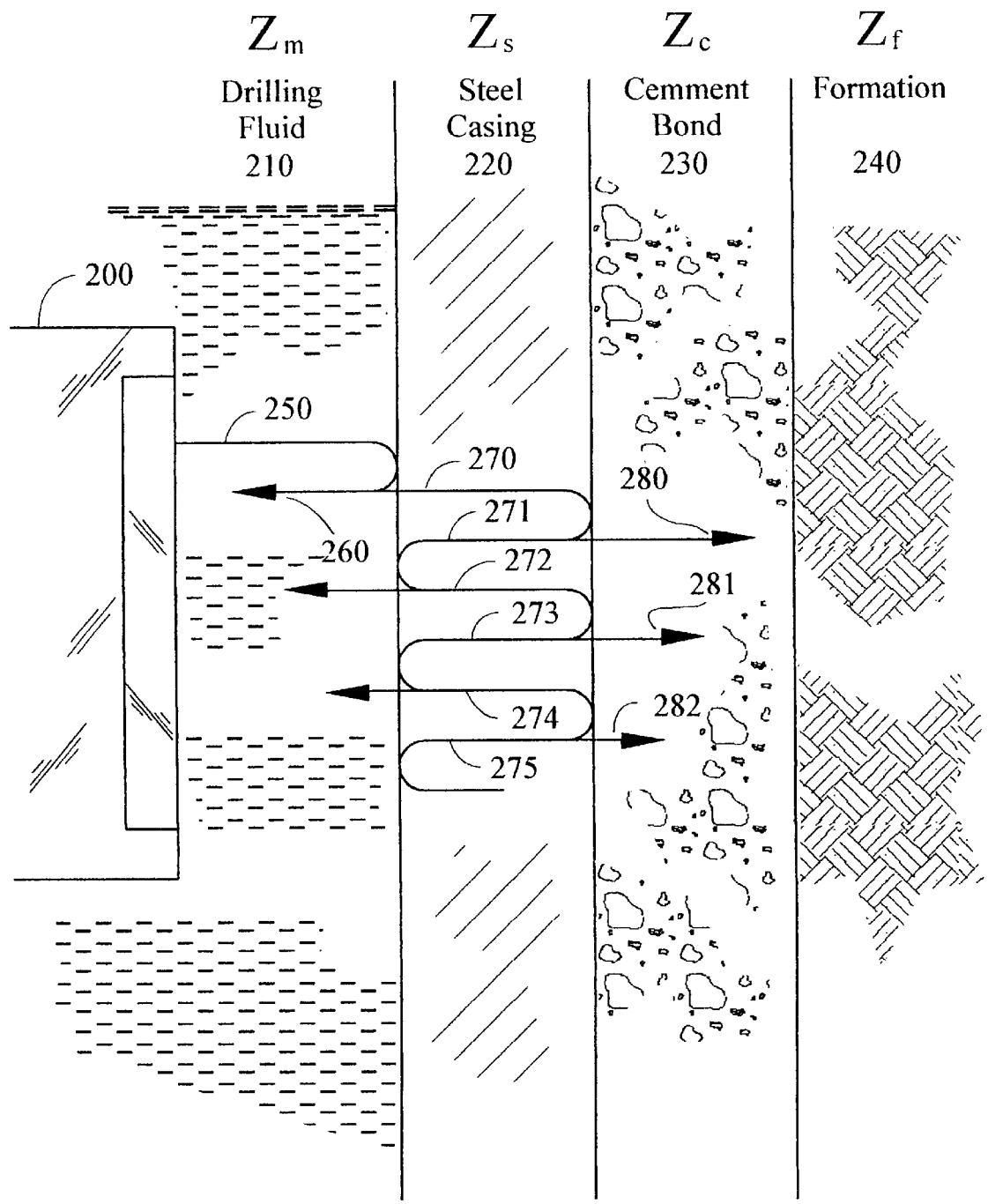
FIG. 2 illustrates waveform reflection and reverberation

FIG. 2 illustrates the acoustic wave path and casing reverberations for a downhole acoustic wave. Shown are acoustic transceiver 200, well fluid 210, steel casing 220, bonding cement 230, and a portion of surrounding formation 240. Acoustic transceiver 200 is part of a wireline device (not shown), while well fluid 210 acts as a transmission medium while occupying the area between the wireline device and the casing, an area referred to as the annulus. Well fluid 210, casing 220, cement 230, and formation 240 each has its own impedance, labeled $Z_m$, $Z_s$, $Z_c$, and $Z_f$, respectively. Also shown is acoustic signal 250, including first reflected portion 260, casing reverberation portions 270, 271, 272, 273, 274, 275 and cement wave portions 280, 281, 282. Reverberations also propagate through the cement due to cement wave portions 280–282, although this is not explicitly shown.

To measure cement impedance, the acoustic transceiver 200 sends out an ultrasonic impulse 250, with a characteristic bandwidth of 195 to 650 kHz, then switches to the receive mode. The impulse frequency should be focused on the expected resonance frequency of the casing. The sound impulse 250 travels through the well fluid 210 and strikes the casing 220. The largest portion of the energy of the impulse is reflected back to the transducer as reflected wave 260 while a small amount of signal enters the casing as wave 270. When the well fluid 210 is water, the reflected wave form has an amplitude of about 93% of the initial impulse. The portion of the signal that entered the casing is reflected back and forth between the casing/annulus interface and the casing/formation interface, as illustrated by wave reverberations 271–275. At each reflection some energy is transmitted through the interface, dependent on the acoustic impedance contrast, and is either directed back toward the transducer or out into the cement. The signal inside the casing is quickly dissipated in this manner at a rate directly dependent on the acoustic impedance of the material outside the casing according to the equation:

$$R_1 = (Z_1 - Z_2)/(Z_1 + Z_2) \quad (1)$$

Where $R_1$ is the reflective coefficient, and $Z_1$ and $Z_2$ are the impedances of the materials at the interface in question.

Figure 3:
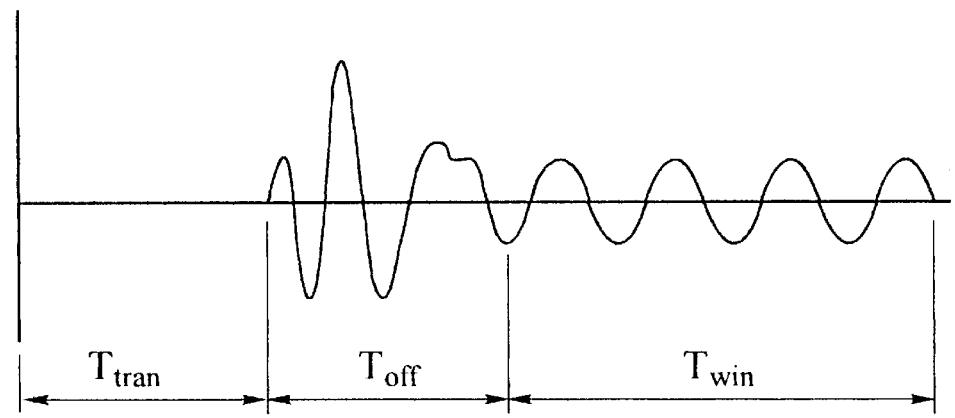
FIG. 3 is a graph showing a received acoustic waveform

The acoustic transceiver 200, now acting as a receiver or transducer, sees a waveform consisting of a loud initial reflection followed by an exponentially decaying signal with peak to peak times equaling twice the travel time through the casing. FIG. 3 illustrates the measured acoustic waveform received at the transceiver 200. If time t=0 is the time of generation of the acoustic wave at the acoustic transmitter, then the time $T_{tran}$ represents the transit time (the time for the travel of this acoustic wave to the casing and its time to return back to the transceiver). As such, the transit time $T_{tran}$ provides an indication of the downhole distance between the acoustic transmitter and the casing wall. Also shown in FIG. 3 are the Time Offset, $T_{off}$, and the Resonance Window, $T_{win}$, both of whose significance is explained below.

Figure 4:
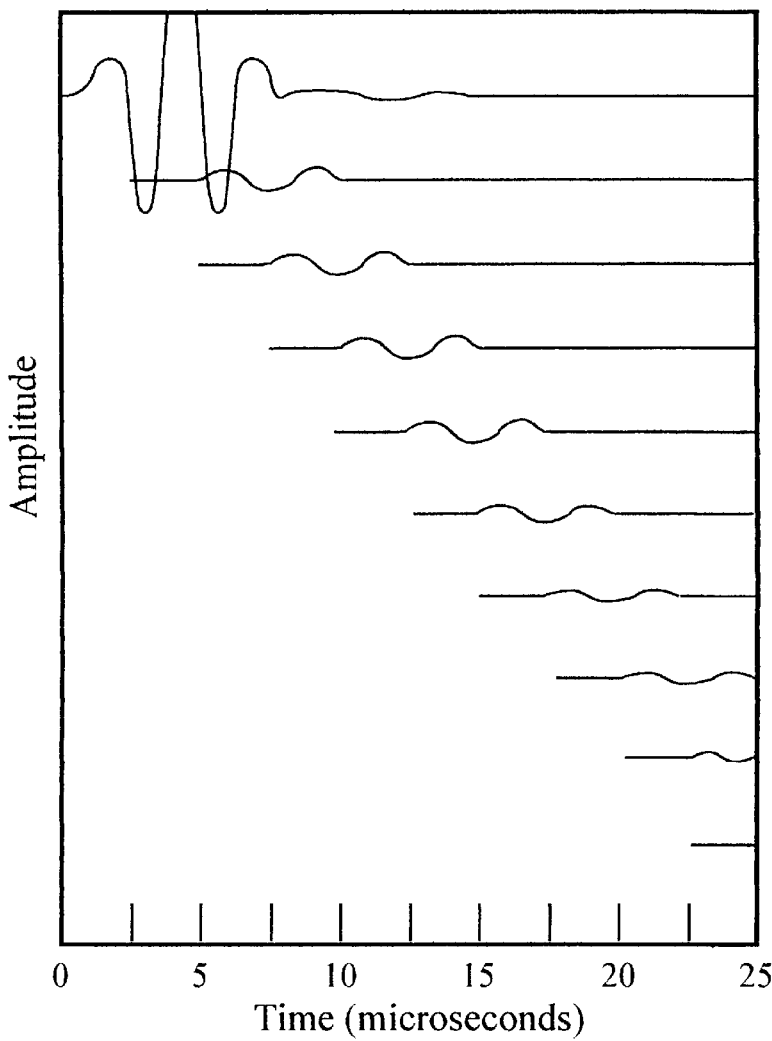
FIG. 4 is a diagram illustrating the component parts of FIG. 3

FIG. 4 illustrates the individual waveforms, both first reflection and reverberations, that sum to provide the waveform of FIG. 3. To find the waveform received by the transducer, each reverberation waveform is added to the initial reflection waveform, with each reverberation being delayed an amount proportional to the width of the casing. Further, because the acoustic transducer is not a perfect transmitter, it "rings" somewhat upon the transmission of an acoustic wave. This transducer "ringing" also is included in the detected waveform, and must be accounted for by the present invention.

Because the cement must be properly bonded around the entire periphery of the casing, it is necessary to determine the impedance of the cement at multiple locations around the circumference of the borehole. Therefore, a downhole acoustic transceiver must transmit greater than one shot or impulse to ensure that a proper bond exists between the casing and the formation around the entire periphery of the borehole. Preferably, an acoustic tool will fire about 100 shots around the circumference of the borehole. Spot size is about 0.4" wide and 1" high. If water is the drilling fluid, a stand-off to 1½" is sufficient, while a more viscous drilling mud requires a smaller stand-off. Because each waveform creates its own wave-train, and each wave-train corresponds to the cement impedance at a particular point along the casing circumference, a substantial amount of data is created for analysis. As such, a mathematically simplified approach is necessary so that cement bonding may be obtained real-time.

Figure 5A:
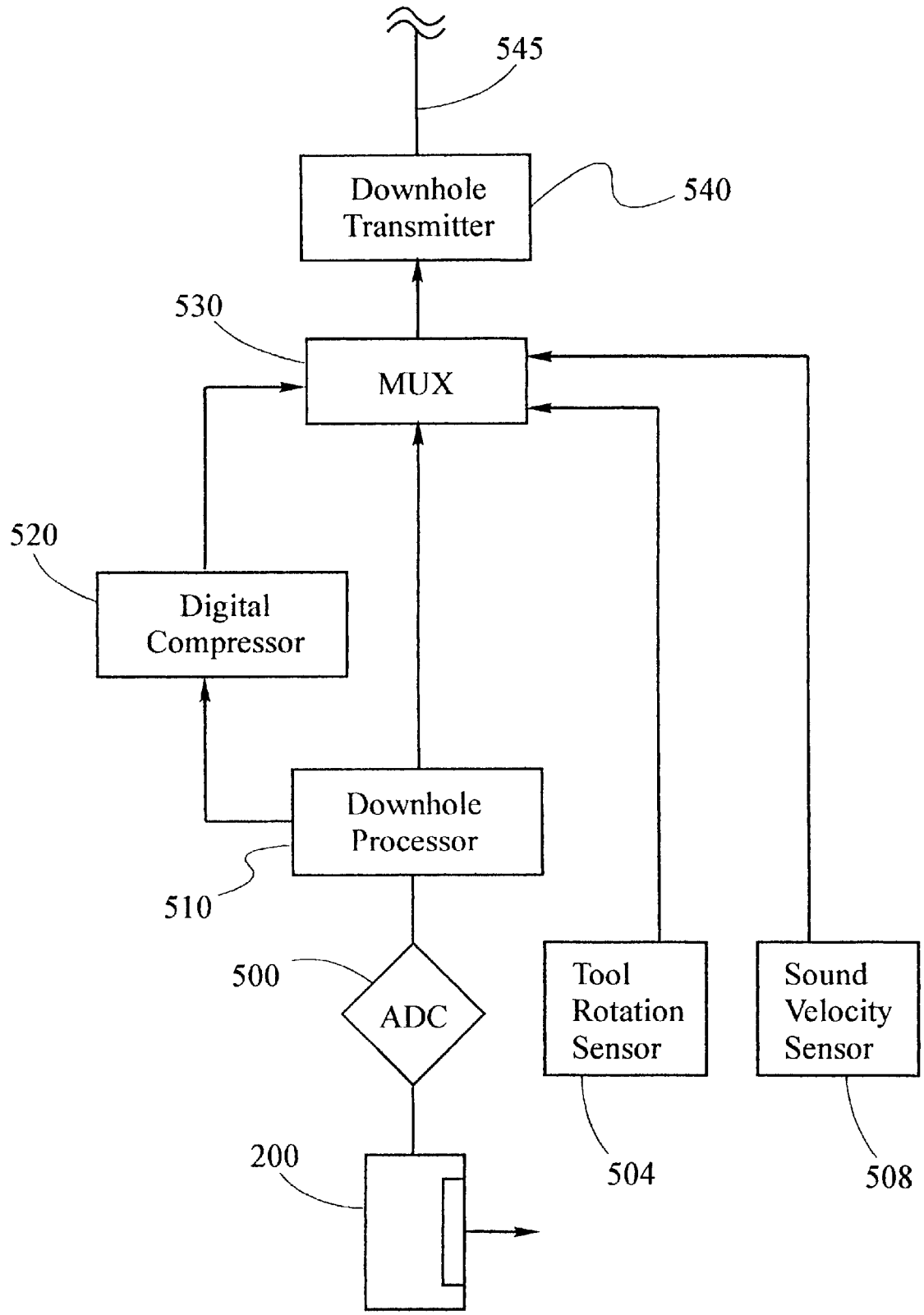
FIG. 5A is a diagram of a subterranean system built in accord with the preferred embodiment
Figure 5B:
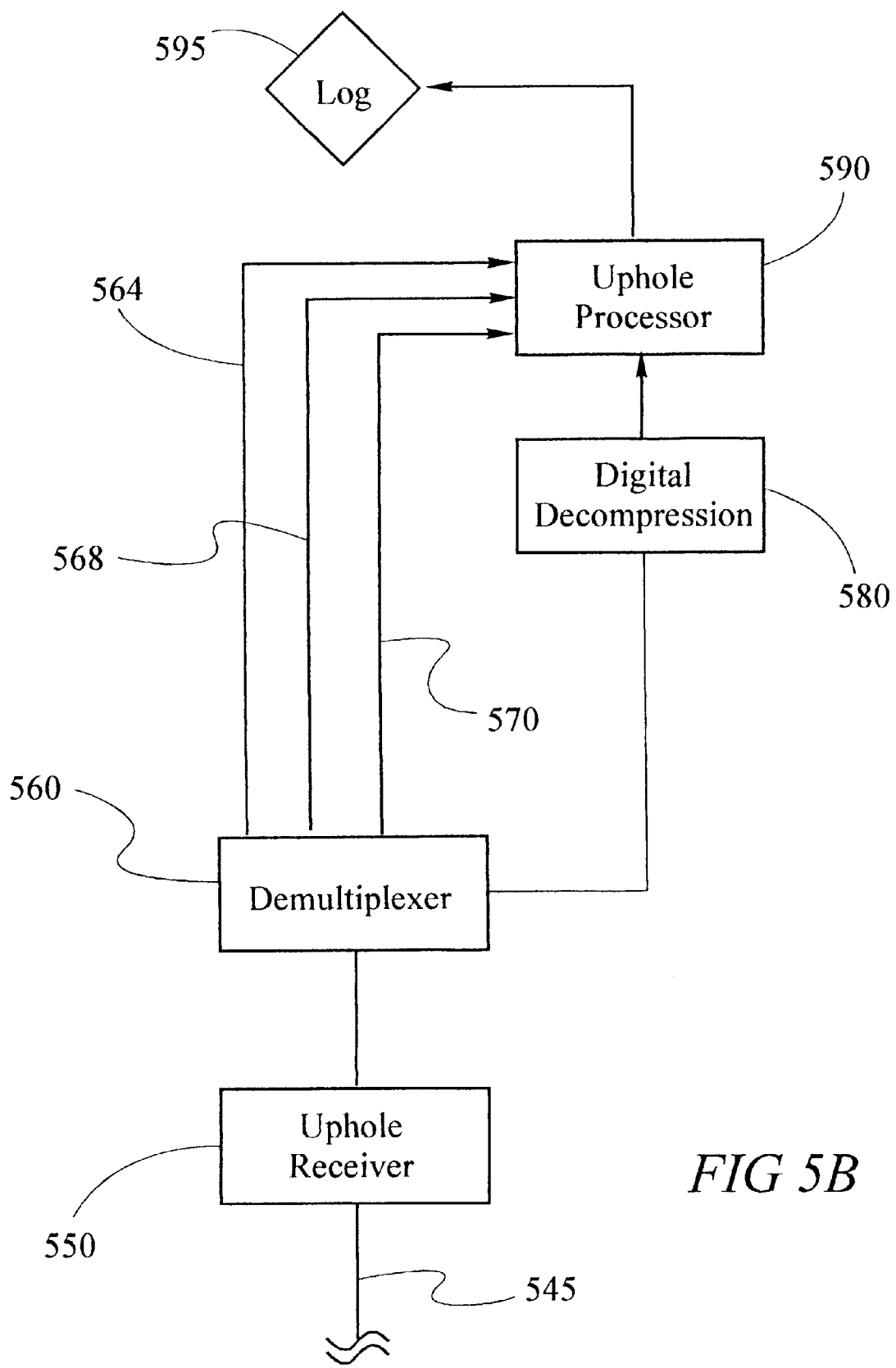
FIG. 5B is a diagram of the above ground system built in accord with the preferred embodiment

FIG. 5 illustrates a device built in accord with the preferred embodiment. Shown in FIG. 5A is acoustic transceiver 200, analog-to-digital converter 500, a tool rotation sensor 504, a tool for measuring the speed of sound in mud 508, a processor 510 for recording start time and gain, waveform decompression chip 520, and multiplexer 530. Waveform decompression chip 520 could alternately be part of a processor. Also shown are downhole transmitter 540 connected to multiplexer 530 and telemetry cable 545. Referring now to FIG. 5B, at the surface are located uphole receiver 550, demultiplexer 560, transmission line 564 carrying tool rotation information to processor 590 for a data log 595, transmission line 568 carrying acoustic mud velocity data to uphole processor 590, transmission line 570 carrying gain and start time information to uphole processor 590, and waveform decompression chip 580. Attached to decompression chip 580 is processor 590. Processor 590 generates data suitable for a log 595.

Referring now to both FIGS. 5A and 5B, high frequency pulse/echo transducer 200 circumferentially collects data of casing reflection and reverberation. This acoustic waveform is digitized by analog-to-digital converter 500 and sent to processor 510, which detects the first reflection from the digitized signal. Processor 510 then computes the relevant start time and transit time. Because the total waveform data are greater than the bandwidth capacity of transmission line 545, digital compression 520 is performed. Suitable compressions include wavelet and ADPCM (Adaptive Differential Pulse Code Modulation) techniques, which work well for smoothly varying data. To minimize compression error, the waveform data should be fed backward for when utilizing the ADPCM algorithm. In addition, tool rotation information and the speed of sound in the transmission fluid are determined. The compressed waveform from digital compression chip 520 is then multiplexed 530 with the tool rotation information and the measured speed of sound in the transmission medium (e.g. mud). Downhole transmitter 540 sends this multiplexed data to the surface. Sending the data to the surface allows processing by faster, more sophisticated machinery.

This multiplexed data is received by uphole receiver 550 and is separated into component parts by demultiplexer 560. Waveform decompression chip 580 provides the reconstructed waveform to processor 590, which also receives start time and mud speed information. Upon the determination of the cement impedance, processor 590 combines this with tool rotation information and creates a log 595.

Figure 6A:
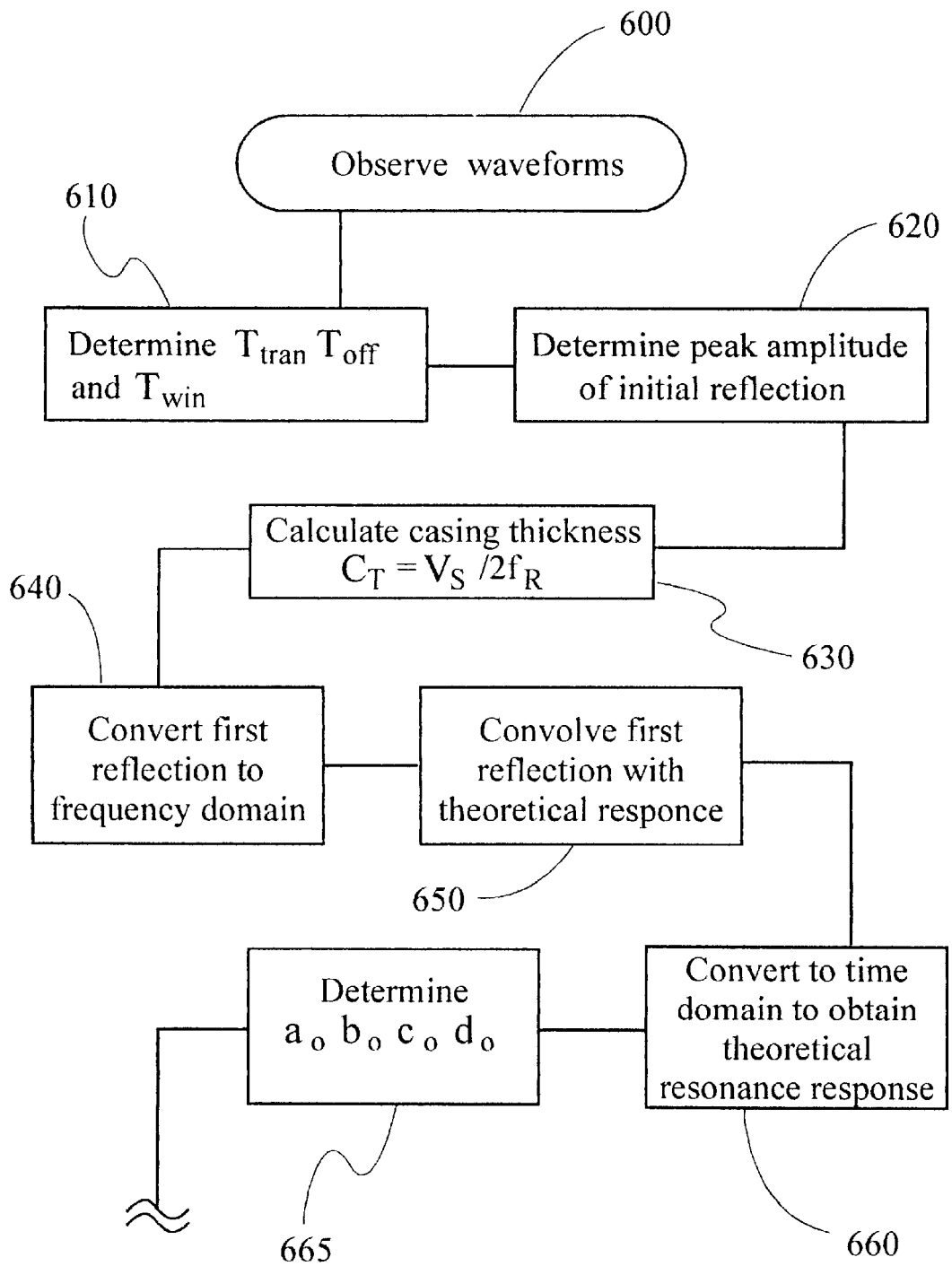
FIG. 6A is a flow diagram of the preferred embodiment
Figure 6B:
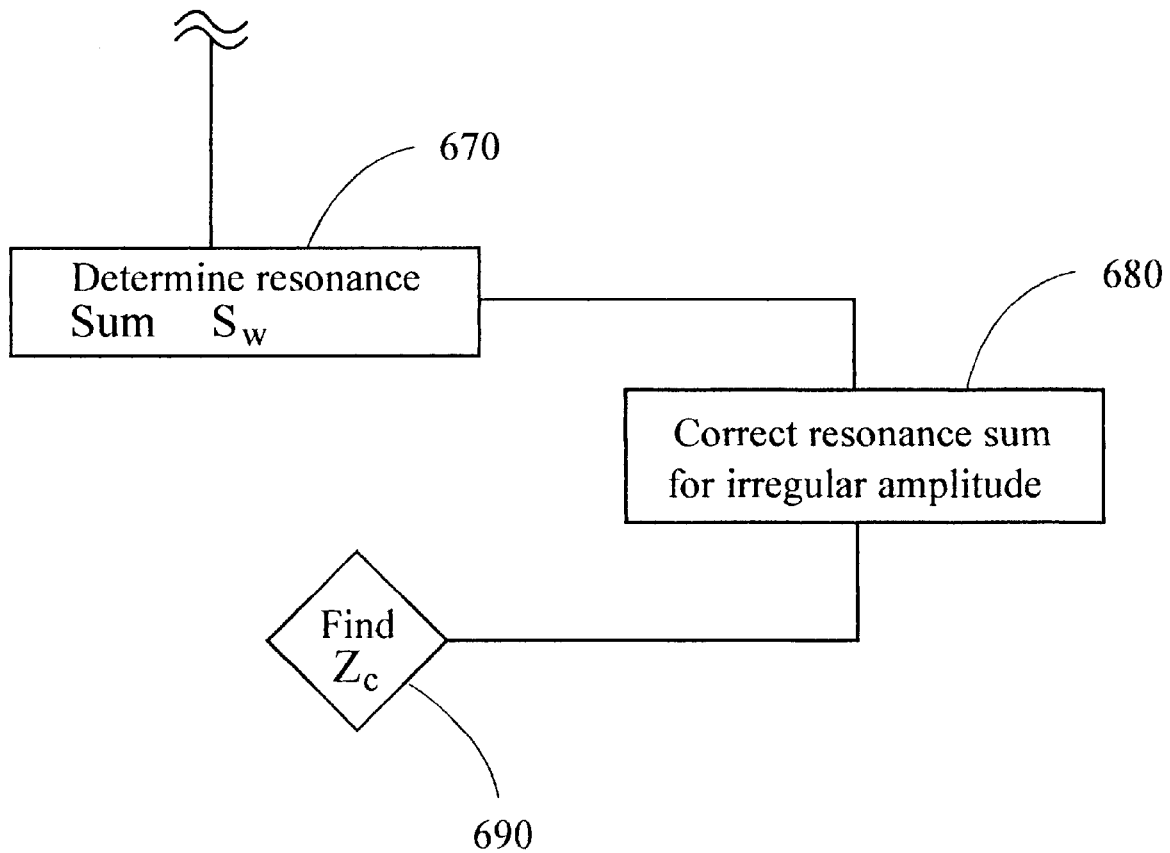
FIG. 6B is a flow diagram of the preferred embodiment

FIG. 6 illustrates a preferred method for the present invention. At step 600, an observed waveform is provided downhole for processing. The waveform's transit time ($T_{tran}$) is obtained at step 610, as well as the time windows $T_{off}$ and $T_{win}$. The definition of transit time was explained above with reference to FIG. 3 and may be easily measured by a first reflection detector portion of processor 510. $T_{off}$ and $T_{win}$ are then selected to obtain a time window $T_{win}$ that contains reliable reverberation information. $T_{off}$, measured from the time of receipt for the initial reflection, is a time window that encompasses the initial reflection. As such, its duration is dependent upon the frequency of the acoustic impulse transmitted by acoustic transceiver 200 and the nature of the drilling fluid. $T_{off}$ also must account for error introduced because of the real-world shortcomings of the acoustic transducer (transducer "ringing"), and thus $T_{off}$ must be slightly longer than if chosen theoretically. Nonetheless, $T_{off}$ is about 15 microseconds. $T_{win}$ is juxtaposed with $T_{off}$ and is a time window of interest because $T_{win}$ contains reverberation information uncontaminated by the first reflection. The duration of $T_{win}$ should be brief enough so that noise and reverberations occurring in the cement 230 do not make unreliable the received casing reverberation waveforms. Nonetheless, so that a reliable wave train containing sufficient data is obtained, $T_{win}$ preferably includes at least four reverberations. Thus, $T_{win}$ is about 12.8 microseconds.

At step 620, the peak amplitude of the initial reflection (contained within $T_{off}$) is determined. One complicating factor when determining the value of the peak amplitude is the digitized nature of the waveform signal received uphole. Further, the waveform data is digitized coarsely (i.e. the digital data points are spaced out widely). As such, undesired error is introduced. To correct the error quickly and accurately with a minimum of processing, the present invention employs a quadratic interpolation approach to approximate closely the amplitude peak of the initial reflection.

Figure 7A:
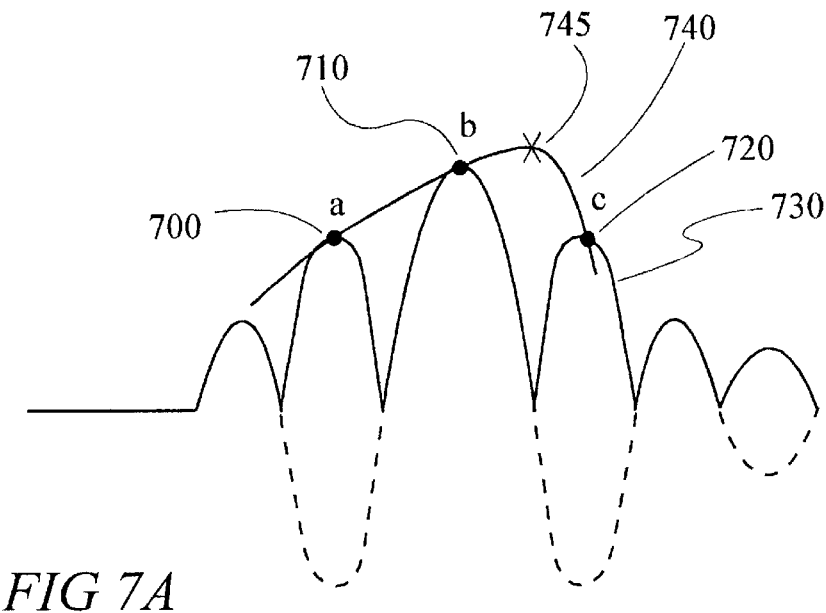
FIG. 7A shows a waveform constructed from three digital data points
Figure 7B:
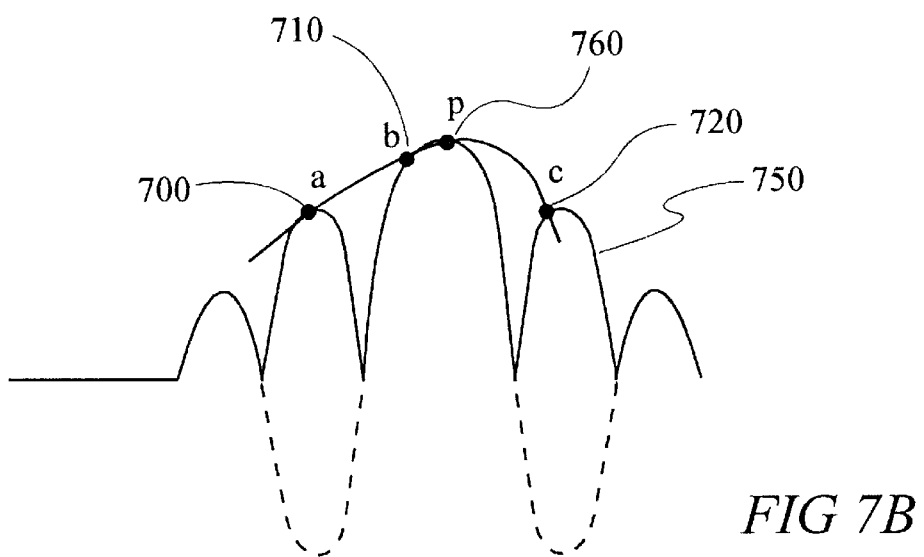
FIG. 7B shows the analog waveform corresponding to three data points

FIG. 7A shows an absolute value digital waveform 730 modeled on three digital data points a, b, and c, labeled 700, 710, and 720, respectively. Quadratic curve 740 including a maximum amplitude point labeled X 745, are also shown. FIG. 7B shows the absolute value analog waveform 750 as detected downhole (corresponding to digital waveform 730). Also illustrated are points a, b, and c, in addition to point p 760, the peak amplitude point of the analog waveform.

Referring back to FIG. 7A, points a 700, b 710, and c 720, are transmitted uphole as part of the digitized and compressed waveform, and these points are then used to construct a waveform 730. However, waveform 730, based on digital data points, is not an exact replica of the analog waveform 740. As shown in FIG. 7B, the absolute maximum amplitude point p of the analog waveform 740 is greater than the amplitude corresponding to point b 710. This effect becomes more pronounced as the digital data sampling becomes more coarse. To account for this error, the present invention uses a quadratic approach based on points a, b, and c to find the actual analog peak. Referring now to both FIGS. 7A and 7B, the peak 745 of the quadratic curve 740 closely approximates the actual peak of the waveform 750, point p 760. Thus, a quadratic approximation based on points a, b, and c may be used uphole to approximate the actual peak of the analog waveform 750.

To approximate the actual peak amplitude with a great degree of precision, three adjacent absolute peaks (a, b, c) must be found, where the magnitude of a is less than b, which in turn is greater then c (a<b>c). Then, points a, b, and c are fit to a quadratic curve 740 having the relationship:

$$Y = A + Bx + Cx^2 \quad (2)$$

By fitting this equation to the known points a, b and c as shown in FIG. 7, the coefficients A, B, and C may be found. The amplitude (y-axis) and time (x-axis) of peak 745 may then be found from the quadratic curve as follows:

Amplitude of peak=$A - B^2/4C$

Time of peak=$-B/2C$

Referring again to FIG. 6A, the casing thickness is found at step 630. Casing thickness may be found according to the relation:

$$C_T = V_s/(2f_R) \quad (3)$$

Figure 8:
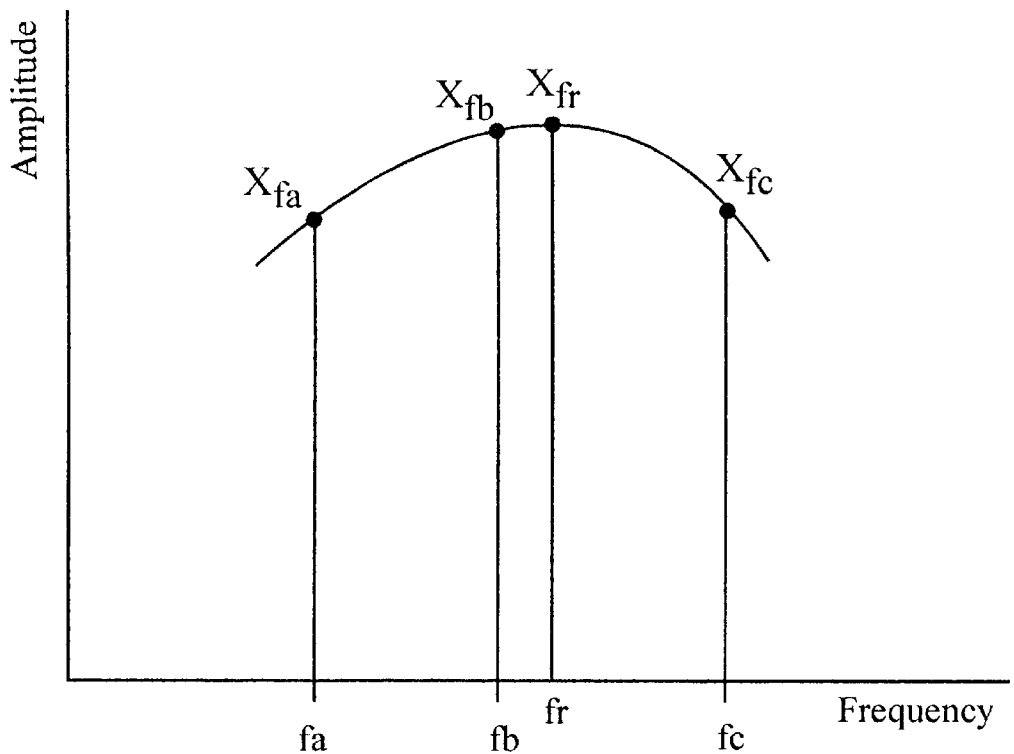
FIG. 8 is a frequency domain illustration of a received waveform

Where, $C_T$=casing thickness $V_s$=the velocity of sound in steel $f_R$=resonance frequency of the casing The velocity of sound in steel, $V_s$, is a known quantity. The resonance frequency of the casing may be obtained as follows. First, the reverberation waveform defined by $T_{win}$ is transformed to the frequency domain by use of DFT (Discrete Fourier Transform). FIG. 8 illustrates a frequency domain graph of such a reverberation waveform. As is well known, the DFT embodies the proposition that a waveform may be represented by an infinite number of sinusoids at varying frequencies. Because resonance frequency is defined as the frequency at which maximum energy is reflected back by the casing, the resonance frequency corresponds to frequency at which peak amplitude is obtained. This frequency is labeled $f_R$. Frequency $f_R$ corresponds to an amplitude point labeled $X_{fR}$. Also shown are frequencies $f_a$, $f_b$, and $f_c$. To find the peak amplitude point $X_{fR}$, an initial guess of resonance frequency is used to establish a first amplitude, $X_{fa}$. By incrementing (if $X_{fa}<X_{fb}$) or decrementing (if $X_{fa}>X_{fb}$) the guess frequency to $f_b$, a second amplitude value $X_{fb}$ is obtained. Upon obtaining a third amplitude $X_{fc}$ satisfying the relationship $X_{fa}<X_{fb}>X_{fc}$, a quadratic approximation may once again be employed to find the amplitude peak $X_{fR}$ and corresponding resonance frequency $f_R$.

The accurate determination of resonance frequency and peak amplitude, combined with the measured digital data, allows an accurate reconstruction uphole of the analog reflection signal 260 contained in $T_{off}$. The accurate reconstruction of the reverberation waveform contained in $T_{win}$ is not as problematic.

Referring back to FIG. 6A, proper modeling applied to the first reflection signal 260, as defined by $T_{off}$, gives a theoretical prediction of what the reverberation waveform contained in $T_{win}$ should look like. To accomplish this, at step 640 the first reflection signal is transformed by Fast Fourier Transform (FFT) into its frequency domain equivalent. This yields $S(\omega)$. Because the modeling is done in the frequency domain, amplitude and phase errors are eliminated. This error elimination simplifies mathematical processing (and hence faster processing is obtained).

Alternately, instead of transforming each first reflection individually, to simplify and speed mathematical processing, the first reflections may first be averaged and the result transformed at step 640 by FFT processing into the frequency domain to yield $S(\omega)$. Further, averaging of the first reflection is preferred because, due to the same transducer collecting all the data along the circumference and the majority of the energy being in the first reflection, most of the transducer properties are in the initial reflection. Thus, the average of the first reflections along the circumference will give a better estimate of the transducer properties, and thus a better input to the theoretical modeling. A most reliable first reflection average may be obtained by discarding first reflections that have amplitudes above or below a preset deviation from a moving average of preceding first reflections (i.e. by discarding those first reflection waveforms that correspond to some type of defect in the casing).

At step 650, a theoretical prediction of the reverberation waves is obtained by convolution of the frequency-domain first reflection signal, $S(\omega)$, with a frequency-domain theoretical response equation, $R(\omega)$. Assuming a flat casing, the theoretical frequency domain response may be modeled by the following:

$$R(\omega) = \frac{Z_m - Z_s}{Z_m + Z_s} + \frac{\frac{4Z_m Z_s}{(Z_m + Z_s)^2} \frac{Z_s - Z_c}{Z_s + Z_c} e^{-i2\omega \frac{C_t}{V_s}}}{\left(1 - \frac{Z_s - Z_m}{Z_m + Z_s} \frac{Z_s - Z_c}{Z_s + Z_c} e^{-i2\omega \frac{C_t}{V_s}}\right)} \quad (4)$$

Where $R(\omega)$=the reflection coefficient for angular frequency $\omega$ $Z_m$, $Z_s$, $Z_c$=impedances for mud, steel casing and cement behind casing $V_s$=the speed of sound in the steel casing Although the casing has a degree of curvature (because it is cylindrical), it may accurately be presumed as a flat surface locally in view of the comparatively short wavelengths of the acoustic signal. This is because the frequency and shape of the transducer, combined with the offset between the transducer and the casing, ensure that the acoustic beam does not spread significantly. For smaller casings, more severe casing curvature may be compensated for by a smaller offset between the transducer and the casing wall, thereby precluding appreciable beam spreading. Only where there are streaks, roughness, or gouges in the casing must the present invention normalize the received waveform, as described below with respect to step 680.

For equation (4), $V_s$ is a well known quantity and $C_T$ has been obtained for a particular waveform at step 630. The use of an average of casing thickness, $C_{Tav}$, may instead be used at step 650. The use of an average of casing thickness helps simplify and speed mathematical processing, making obtainable real time derivations. The use of $C_{Tav}$ is also preferred because casing thickness does not vary significantly along an azimuth. As such, average casing thickness is the best estimate available to calculate the coefficients $a_0$, $b_0$, $c_0$, and $d_0$, explained below. $Z_m$ may be obtained upon determining $V_m$, the speed of sound in mud, by use of the following relationship:

$$Z_m = V_m \rho \quad (5)$$

Where, $Z_m$=impedance of the transmission medium (mud)

$V_m$=velocity of an acoustic wave in the transmission medium $\rho$=density of the transmission medium Methods to determine $\rho$ by measurement, and $V_m$ by tool measurement 508, are well known.

At step 660, these results are transformed back into the time domain by use of an Inverse Fast Fourier Transform (IFFT). As such, step 660 provides the theoretical reverberation response for the observed initial reflection waveform(s) in the time domain, the theoretical resonance sum being represented with the upper case notation $$\sum |X_t|.$$

This theoretical reverberation response, obtained at step 660, is used as a yardstick for the observed reverberation waveform contained in $t_{win}$.

Next, four unknowns are obtained at step 665. As an initial matter, for a reverberation window of interest, $T_{win}$, the natural log of the sum of the reverberation waveform amplitude varies linearly with cement impedance. That is, a linear relationship between cement impedance and $S_w$ may be expressed as:

$$Z_c = A + B \ln(S_w) \quad (6)$$

where $S_w$ is the sum of the reverberation waveform amplitudes and has the form:

$$S_w = \sum |x_t| \quad (7)$$

the lower case $X_t$ being the amplitude at any given point in the observed reverberation waveform contained in $T_{win}$. If, $$A = a_0 + b_0 C_t \quad (8)$$

$$B = c_0 + d_0 C_t \quad (9)$$

then equation (6) may be expressed as:

$$Z_c = a_0 + b_0 C_t + c_0 \ln(S_w) + d_0 C_t \ln(S_w) \quad (10)$$

Where $Z_c$ is the cement impedance behind the casing.

Substituting the theoretical resonance sum $$\sum |X_t|$$

in lieu of $S_w$, the right side of equation (10) contains $C_t$ and four unknowns: $a_0$, $b_0$, $c_0$, and $d_0$. At step 665, these four coefficients are determined by proper substitution and use of the well known least square approximation technique. More specifically, the determination of four unknowns, $a_0$, $b_0$, $c_0$, and $d_0$, requires at least four equations. A higher order approximation for the values of $a_0$, $b_0$, $c_0$, and $d_0$ may be obtained by the use of more than four equations. For example, the values 1, 4, and 8 may variously be introduced as values for $Z_c$, and $C_{Tav}+/-dC_{Tav}$ as established at step 630 may be substituted for three values of $C_t$. The magnitude of $dC_{Tav}$ is about 0.025 inches. These substitutions, then, yield nine equations. Use of the well known least square approximation techniques yields accurate estimates of $a_0$, $b_0$, $c_0$, and $d_0$.

Next, the actual resonance sum $S_w$ is obtained at step 670. As defined above:

$$S_w = \sum |x_t|$$

where the lower case $x_t$ is the observed/measured amplitude at any given point in the reverberation waveform.

Figure 9:
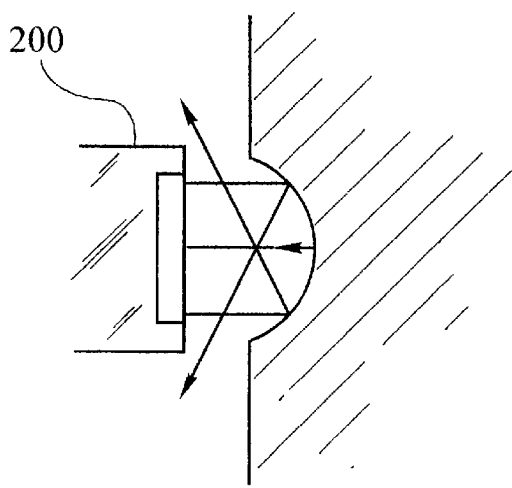
FIG. 9 illustrates the energy deflection of a first gouge in the casing wall
Figure 10:
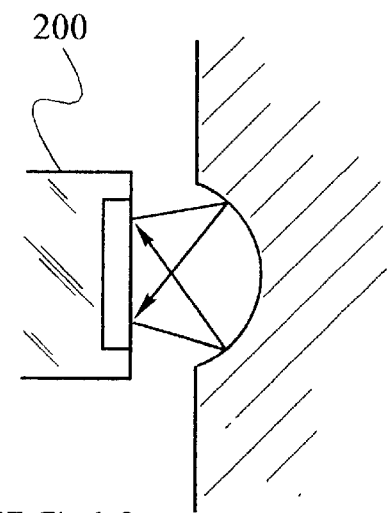
FIG. 10 illustrates the energy deflection of a second gouge in the casing wall

However, scratches, roughness, and gouges can affect the detected reverberation waveform. For example, a gouge such as that shown in FIG. 9 can reduce the amount of energy detected by the transducer 200. A gouge such as that shown in FIG. 10 can increase the amount of energy detected by the transducer 200. Such errors could lead to an indication of a free pipe when, in truth, a good bond is present, or vice versa.

Figure 11:
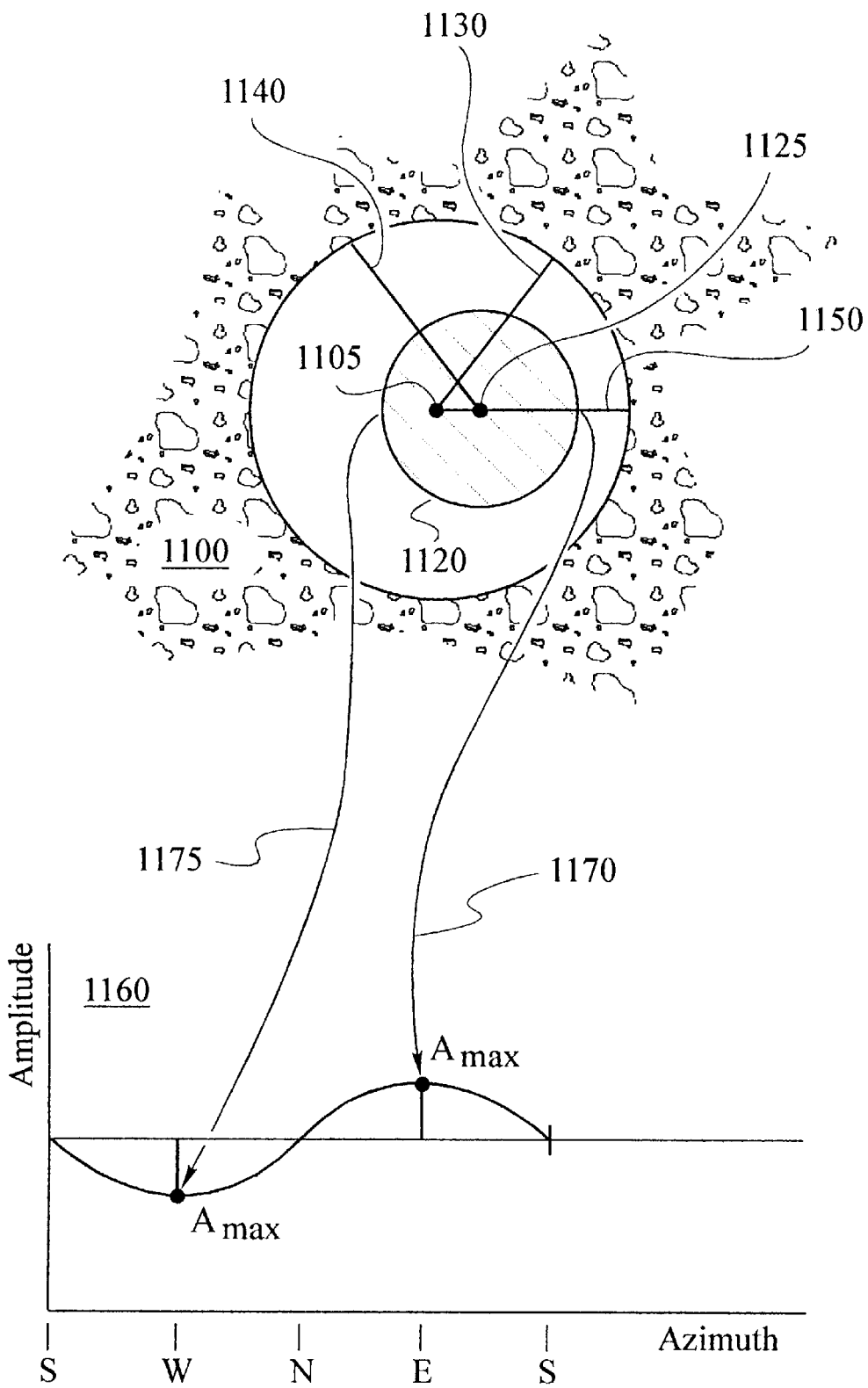
FIG. 11 illustrates an off-center casing with respect to the wellbore

Other conditions also lead to similarly misleading initial reflections, such as a non-circular casing (not shown), or the tool being off-center with respect to the borehole, shown in FIG. 11. The circular geometry or lack thereof for the casing may be established by a comparison of transit times for the initial reflection, $T_{tran}$.

FIG. 11 includes a wellbore 1100, casing 1120 in wellbore 1100, a well bore center point 1105, and a casing center point 1125. Also shown are normal lines 1130, 1140 and 1150; normal line 1130 originates from wellbore center point 1105, normal line 1140 originates from casing center point 1125, and normal line 1150 travels through both center points 1105 and 1125. Graph 1160 includes amplitude and azimuth axis. Lines 1170 and 1175 correlate the two normal coincidence angles and the two maximum amplitude points $A_{max}$.

Where the casing is off-center with respect to the borehole, the initial reflection amplitude will be highest when both normal lines coincide, such as at normal line 1150. Otherwise, the amplitude is decreased. As such, a sine wave amplitude pattern emerges, with the amplitude peaks occurring where the normal lines coincide. This phenomenon may be used to identify the off-center casing with respect to the wellbore. Thus, the present invention corrects for the presence of irregularities in and around the casing to obtain optimum impedance measurement accuracy.

The resonance sum is corrected to account for defects at step 680. This is complicated because based upon a single observation, it is extremely difficult to determine whether the casing has a defect. Further, the presence of a casing defect is most apparent from examination of the initial reflection. As such, to help determine whether a defect exists, the initial reflection waveform is compared to a moving average of a number of previous reflection amplitude measurements. In other words, a moving average filter using a limited number (e.g. five) of immediately previous measurements is compared to the received initial reflection. If the received waveform amplitude differs more than a preset amount from this moving average, a correction for irregular peak amplitude is necessary. The initial reflection waveform is corrected by normalizing its amplitude to that of the moving average. This yields the magnitude of the correction for the initial reflection waveform. The amount of correction necessary for the resonance sum may be established based on a linear relation. That is, the amplitude of a resonance sum is directly proportional to the peak amplitude of the first reflection variation with respect to the average peak amplitude. As can be readily understood, as the initial waveform amplitude is normalized in a particular direction, the resonance sum is likewise adjusted. For example, if the first reflection peak amplitude is ½ the average peak amplitude, the resonance sum must be corrected by doubling its original value. So that subsequent resonance sums are accurately corrected, any significantly different amplitude initial reflection waveform should be left out of the computations for subsequent moving averages. Lastly, at step 690, $S_w$ is substituted into equation (10), and cement impedance $Z_c$ is determined for any point along the circumference of the casing.

While preferred embodiments of this invention have been shown and described, modifications thereof can be made by one skilled in the art without departing from the spirit or teaching of this invention. The embodiments described herein are exemplary only and are not limiting. Many variations and modifications of the system and apparatus are possible and are within the scope of the invention. Accordingly, the scope of protection is not limited to the embodiments described herein, but is only limited by the claims that follow, the scope of which shall include all equivalents of the subject matter of the claims.

What is claimed is:

1. A method for determining casing bond impedance, comprising:
   (a) generating an acoustic signal within a borehole casing, said casing having a bond impedance;
   (b) receiving reflections of said acoustic signal from said casing, said reflections comprising an initial reflection portion and a reverberation portion; and
   (c) analyzing said reverberation portion to determine said bond impedance, said analyzing of said reverberation portion including obtaining a theoretical reverberation portion and using said reverberation portion with said theoretical reverberation portion as a basis to determine said casing bond impedance.

2. The method of claim 1, wherein said analyzing step is a step for analyzing said reverberation portion.

3. The method of claim 1, wherein a value for said bond impedance at a given location is obtained real time.

4. The method of claim 1, wherein said step of analyzing said reverberation response includes using a theoretical reverberation response as a basis for determining said casing bond impedance.

5. The method of claim 1, wherein said theoretical reverberation portion is obtained by convolving said initial reflection portion with a theoretical reverberation transfer function.

6. A method for determining the impedance of a bond between a borehole casing and a borehole wall, comprising:
   (a) providing a signal corresponding to a reflected wave form, said reflected wave form having an initial reflection portion and a reverberation portion;
   (b) transforming the initial reflection portion of said signal to frequency domain;
   (c) convolving said frequency-domain initial reflection portion with a theoretical frequency-domain response model;
   (d) converting the result of step (c) to time domain to obtain a time-domain theoretical reverberation response;
   (e) determining from said theoretical reverberation response and said reverberation portion of said signal an impedance value corresponding to said bond between said borehole casing and said borehole wall.

7. The method of claim 6, wherein said transforming step utilizes a fast Fourier transform.

8. The method of claim 6, wherein said signal of said providing step is a digitally compressed wave form.

9. The method of claim 8, wherein said digitally compressed wave form is compressed by use of the adaptive differential pulse code modulation technique, and wherein said wave form data is fed backward before being compressed.

10. The method of claim 8, wherein said digitally compressed signal is reconstructed by finding the quadratic approximation of the peak amplitude and the resonance frequency of said signal corresponding to said reflected wave form.

11. The method of claim 6, wherein said theoretical frequency-domain response model is according to the equation:

$$R(\omega) = \frac{Z_m - Z_s}{Z_m + Z_s} + \frac{\dfrac{4Z_m Z_s}{(Z_m + Z_s)^2} Z_s - \dfrac{Z_c}{Z_s + Z_c}}{\left(1 - \dfrac{Z_s - Z_m}{Z_m + Z_s}\dfrac{Z_s - Z_c}{Z_s + Z_c} e^{-i2\omega \frac{C_t}{V_s}}\right)} e^{-i2\omega \frac{C_t}{V_s}}$$

Where $R(\omega)$=the reflection coefficient for angular frequency $\omega$ $Z_m$, $Z_s$, $Z_c$=impedances for mud, steel casing and cement behind casing $V_s$=the speed of sound in the steel casing $C_t$=casing thickness $V_s$=the velocity of sound in steel.

12. The method of claim 11, wherein average casing thickness is used in lieu of $C_t$.

13. The method of claim 6, wherein said determining step involves calculating coefficients according to the following equation:

$$Z_c = a_0 + b_0 C_t + c_0 \ln(S_w) + d_0 C_t \ln(S_w)$$

Where
- $Z_c$=impedance for cement behind casing
- $S_w$=the sum of the reverberation waveform amplitudes
- $C_t$=casing thickness
- $a_0, b_0, c_0, d_0$=coefficients.

14. The method of claim 13, wherein $a_0$, $b_0$, $c_0$, and $d_0$ are determined by the least square approximation technique.

15. The method of claim 6, wherein said determining step includes correcting for an irregular first reflection peak amplitude before determining said impedance.

16. The method of claim 6, wherein said transforming step includes averaging a plurality of first reflection portions from a plurality of signal wave forms.

17. The method of claim 16, wherein said averaging said plurality of first reflection portions from said plurality of signal wave forms includes discarding any first reflection portion that deviates more than a preset amount from an average of the remainder of said plurality of said first reflection portions.

18. The method of claim 6, wherein said providing step is a step for providing a signal corresponding to a reflected wave form.

19. The method of claim 6, wherein said transforming step is a step for transforming the initial reflection portion of said signal to frequency domain.

20. The method of claim 6, wherein said convolving step is a step for convolving said frequency-domain initial reflection portion with a theoretical frequency-domain response model.

21. The method of claim 6, wherein said converting step is a step for converting the result of step (c) to time domain.

22. The method of claim 6, wherein said determining step is a step for determining from said theoretical reverberation response and said reverberation portion of said signal an impedance value.

23. The method of claim 6, wherein said determining step involves calculating coefficients.

24. A processor adapted to provide real-time estimates of casing bond impedance, comprising:
- an input terminal configured to receive a data signal, said data signal corresponding to a reflected acoustic wave;
- a processing portion programmable to separate said data signal into a first reflection portion and a resonance portion, said processing portion including a transformation portion programmable to transform mathematically said first reflection portion so that it may be convolved with a response equation to yield a theoretical reverberation response.

25. The processor of claim 24, wherein said transformation portion is programmed according to the equation:

$$R(\omega) = \frac{Z_m - Z_s}{Z_m + Z_s} + \frac{\frac{4 Z_m Z_s}{(Z_m + Z_s)^2} Z_s - \frac{Z_c}{Z_s + Z_c}}{\left(1 - \frac{Z_s - Z_m}{Z_m + Z_s} \frac{Z_s - Z_c}{Z_s + Z_c} e^{-i 2\omega \frac{C_t}{V_s}}\right)} e^{-i 2\omega \frac{C_t}{V_s}}$$

Where,
- $R(\omega)$=the reflection coefficient for angular frequency $\omega$
- $Z_m$, $Z_s$, $Z_c$=impedances for mud, steel casing and cement behind casing
- $V_s$=the speed of sound in the steel casing
- $C_t$=casing thickness
- $V_s$=the velocity of sound in steel.

26. The processor of claim 24, further comprising a value determination portion programmable to calculate an impedance corresponding to the bond between a borehole casing and a borehole wall by inferring said impedance based on a theoretical reverberation response and a measured reverberation response.

27. The processor of claim 26, wherein said value determination portion is programmed according to the equation:

$$Z_c = a_0 + b_0 C_t + c_0 \ln(S_w) + d_0 C_t \ln(S_w)$$

Where
- $Z_c$=impedance for cement behind casing
- $S_w$=the sum of the reverberation waveform amplitudes
- $C_t$=casing thickness
- $a_0, b_0, c_0, d_0$=coefficients.

28. The processor of claim 24, wherein said processor is included in a system further comprising an acoustic transmitter and an acoustic receiver.

29. The processor of claim 24, wherein said processor is a means for processing an acoustic downhole signal to yield a real-time indication of casing bond impedance.

30. A method of analyzing an acoustic signal, comprising:
  (a) generating an acoustic signal by a first transducer, said acoustic signal being suitable for reflection from a borehole casing;
  (b) receiving said acoustic signal at a second transducer, said first and second transducers appropriately but not necessarily being the same, said second transducer generating at least one electrical transducer response waveforms;
  (c) separating said electrical transducer response waveforms into a first portion and a second portion;
  (d) convolving said first portion with a response equation to obtain a theoretical second portion;
  (e) comparing said second portion with said theoretical portion to establish the casing bond impedance for said borehole casing.

31. The method of claim 30, further comprising converting said first portion to the frequency domain prior to said convolving and transforming said theoretical second portion to the time domain prior to said comparing of said second portion with said theoretical portion.

32. The method of claim 30, wherein said comparing includes fitting a mathematical equation to said theoretical portion, establishing values for a set of equation coefficients for said mathematical equation, and applying said values for said set of equation coefficients to said second portion.

* * * * *